(12) United States Patent
Huang et al.

(10) Patent No.: US 7,795,401 B2
(45) Date of Patent: Sep. 14, 2010

(54) MODIFIED HEMOGLOBIN WITH ALLOSTERIC EFFECTOR CONJUGATED

(75) Inventors: Kuang-Tse Huang, Min-Hsiung (TW); Yen-Lin Lin, Min-Hsiung (TW)

(73) Assignee: National Chung Cheng University, Min-Hsiung, Chia-Yi County (TW)

( * ) Notice: Subject to any disclaimer, the term of this patent is extended or adjusted under 35 U.S.C. 154(b) by 910 days.

(21) Appl. No.: 11/515,863

(22) Filed: Sep. 6, 2006

(65) Prior Publication Data

US 2008/0064855 A1    Mar. 13, 2008

(51) Int. Cl.
*A61K 35/14* (2006.01)
(52) U.S. Cl. .................. 530/385; 530/332; 530/350; 530/300; 435/7.1
(58) Field of Classification Search .......... None
See application file for complete search history.

(56) References Cited

U.S. PATENT DOCUMENTS

| 4,670,417 A | 6/1987 | Iwasaki et al. |
| 5,234,903 A | 8/1993 | Nho et al. |
| 5,312,808 A | 5/1994 | Shorr et al. |
| 6,017,943 A | 1/2000 | Acharya et al. |
| 7,501,499 B2 * | 3/2009 | Acharya et al. ............. 530/402 |

OTHER PUBLICATIONS

Wells, Biochemistry, vol. 29, pp. 8509-8517, 1990.*

* cited by examiner

*Primary Examiner*—Hope A Robinson
(74) *Attorney, Agent, or Firm*—Birch, Stewart, Kolasch & Birch, LLP

(57) ABSTRACT

The present invention relates generally to a modified hemoglobin with an allosteric effector conjugated which is capable of dynamically regulating the efficiency of oxygen release. The hemoglobin composition provided in the present invention is utilizing maleimide-Polyethylene glycol-N-hydroxysuccinimidyl as a linker to crossbridge the peptide comprising SEQ ID NO: 1 to the surface of a hemoglobin, and hence, it is able to decrease the oxygen affinity through the characteristic of the peptide which could enter into the central cavity formed between β-β chains of hemoglobin under an appropriate oxygen concentration.

5 Claims, 4 Drawing Sheets

MODIFIED HEMOGLOBIN WITH ALLOSTERIC EFFECTOR CONJUGATED

BACKGROUND OF THE INVENTION

1. Field of the Invention

The present invention relates to a hemoglobin composition, particularly relates to a modified hemoglobin composition, which is capable of dynamically regulating the efficiency of oxygen release.

2. The Prior Arts

The hemoglobin (Hb) is a primary carrier for transporting oxygen in the blood. The hemoglobin contained in human body is a kind of tetramer consisting of two α subunits and two β subunits, which are non-covalently bonded. The molecular weight of each subunit, consisting of one α chain or β chain together with one heme, is about 16,000 daltons. The heme molecule comprises one bivalent ferrous ion for either associating with oxygen molecules, or releasing oxygen molecules to cells under appropriate circumstances.

Although free hemoglobin has the function of carrying oxygen molecules, it still couldn't be a substitute as blood and directly put into human body. The reason lies on that free hemoglobin in a low concentration easily tends to dissociate from tetramer into dimers in human body, where the hemoglobin dimers will conjugate with haptoglobin in blood and then be degraded in liver, and hence decreasing the concentration of haptoglobin. However, when under higher concentration of free hemoglobin, it is not only the above-mentioned metabolism problems arisen, the excessive amount of hemoglobin dimers wouldn't be metabolized thoroughly by liver, and under this circumstance, part of the hemoglobin dimers will be transferred to kidney for metabolism, and hence easily result in the renal dysfunction as well, or even cause renal tubular obstruction due to the passage of hemoglobin dimers through renal corpuscles.

On the other hand, when unmodified hemoglobin has been transfused into human body, it will be spread into the spaces between endothelium and smooth muscle cells and react with nitric oxide therein, and consequently result in the decrease of the concentration of nitric oxide which is capable of activating the soluble guanylyl cyclase (sGC) contained in smooth muscle cells, and thus can't afford sufficient amount of cyclic GMP (cGMP) during metabolic processes. As a result of the shortage of cGMP, the concentration of calcium ions will be unable to be regulated via ion channels and hence accumulated in cells instead. Furthermore, the high concentration calcium ions stocked in cells will also cause the blood vessel contraction as well as result in high blood pressure consequently.

With regard to the resolutions to overcome the critical physiological defects above-mentioned of the hemoglobin with unmodified conformation, while referring to known skills, it is found that most of them are to crosslink either among peptide chains of each subunit or among hemoglobin molecules, or try the method to prevent the dissociation from hemoglobin tetramers. Among them, the familiar inventions for hemoglobin modification, such as U.S. Pat. No. 4,670,417, No. 5,234,903, No. 5,312,808 and No. 6,017,943, polyethylene glycol (PEG) in which are utilized to crossbridge hemoglobin molecules. In addition, some inventions are focusing on the improved skills by utilizing dextran, hydroxyethyl starch, inulin or polyvinylpyrrolidone for hemoglobin crosslinkage, or even encapsulating the hemoglobin into the liposome. Those inventions described above are either capable of crosslinking or aggregating the hemoglobin molecules in order to obtain larger molecules, so that it is applicable to prevent hemoglobin tetramer from being dissociated into dimers and thus won't have side effects of renal function, high blood pressure etc. resulted due to the dissociation from tetramers into dimers as well as spread into spaces between endothelium and smooth muscle cells. Besides, owing to the larger molecular weight and tetramer conformation, the modified hemoglobin would have some advantages such as retarding the decomposition reaction by the protease, and prevent rapid clearance by human body at the same time.

Whereas the prior inventions utilized the methods of crosslinking among hemoglobin molecules or crosslinking peptide chains within each hemoglobin molecule so as to form a larger and more stable molecule to maintain a conformation of hemoglobin tetramer or hemoglobin polymer in order to eliminate side effects of renal function, high blood pressure, they did affect the original conformation of hemoglobin after crosslinking process and then further affect the efficiency of oxygen affinity as well as cooperative effect under normal condition, and thus dramatically decrease both the efficiency of oxygen transportation and providing consequently. On the other hand, the prior hemoglobin solution only has the hemoglobin molecules, excluding other regulatory factors, for instance, 2,3-diphosphogylcerate (2,3-DPG), which is able to bind to the oxygen-carrying hemoglobin and transform which into T state stably. Therefore, if this kind of hemoglobin solution is being used upon blood transfusion, the hemoglobin herein won't be able to release oxygen appropriately while under some circumstance, and thus be impossible to meet the requirement of appropriate efficiency of oxygen supply while under regular circumstance.

SUMMARY OF THE INVENTION

For improving the critical defects of the known technology, namely the side effects such as renal function, high blood pressure etc., where it simply utilize the hemoglobin solution to replace the blood plasma upon the blood transfusion, and the hemoglobin would be easily dissociated from tetramer into dimer, the present invention herein provides a hemoglobin composition having either a intra-crosslinked hemoglobin molecule in which the peptide chains of the subunits are crosslinked or inter-crosslinked hemoglobin molecule in which a plurality of hemoglobin molecules are crosslinked, so that each subunit of such hemoglobin is linked together through covalent bonding and hence prevent the hemoglobin from being dissociated into dimers, therefore it is able to further keeping the above-mentioned side effects away by preventing dimers from spreading into the space between the endothelium and the smooth muscle cells. Meanwhile, due to the larger molecule weight as hemoglobin tetramer (or polymer) provided by the present invention, it will not only increase the viscosity of hemoglobin solution, but also enhance the release rate of nitric oxide by increasing the shear stress applied to endothelium. Moreover, owing to the polyethylene glycol contained in the modified hemoglobin, the hemoglobin composition provided herein also has an advantage of retarding the decomposition by protease so as to preventing rapid clearance from the body.

Another crucial objective of the present invention is to provide a hemoglobin composition which is capable of regulating the oxygen release efficiency by linking a peptide, which comprises the amino acid sequence as an allosteric effector, to the hemoglobin via polyethylene glycol derivatives (hereinafter referred to as PEG derivatives). As the characteristic of said hemoglobin composition, in which the conjugated peptide is able to enter into the central cavity formed between β-β chains of the hemoglobin under a low oxygen concentration, the modified hemoglobin provided by the present invention can increase the oxygen release efficiency under an appropriate circumstance, and further improve the efficiency in both the utilization and transportation of oxygen accordingly.

In light of the above objectives, the present invention intends to provide a modified hemoglobin with an allosteric effector conjugated, which comprising: a hemoglobin composition (namely the [Peptide-PEG-hemoglobin]) prepared by conjugating a peptide comprising SEQ ID NO: 1 on a hemoglobin through a maleimide-PEG-N-hydroxysuccinimidyl; wherein, the peptide comprising SEQ ID NO: 1 is bonded via the cysteine residue therein through the maleimide functional group contained in the maleimide-PEG-N-hydroxysuccinimidyl, and the hemoglobin is bonded via the lysine residue on the surface thereof through the N-hydroxysuccinimidyl functional group contained in the maleimide-PEG-N-hydroxysuccinimidyl.

Additionally, the lysine residue positioned on the outer surface of said hemoglobin for crosslinkage is belonged to the βchain of the hemoglobin, and particularly is but not limit to the 95th amino acid of the βchain. With the effects provided by the peptide contained in the modified hemoglobin with an allosteric effector conjugated, namely the [Peptide-PEG-hemoglobin], in accordance with the present invention, it will be applicable to achieve the objective in regulating the oxygen release rate of the hemoglobin consequently.

On the other hand, the present invention is further able to utilize another PEG derivative, such as succinimidyl propionate-PEG-succinimidyl propionate (hereinafter referred to as SPA-PEG-SPA), to polymerize the described modified hemoglobin, [Peptide-PEG-hemoglobin], with other modified or unmodified hemoglobin so as to form a covalent bonded hemoglobin tetramer (by intra-crosslinking) or a hemoglobin composition with a plurality of polymerized hemoglobin molecules (by inter-crosslinking). The covalent bonded hemoglobin tetramer will prevent four subunits of hemoglobin from dissociation. The hemoglobin tetramer or polymer with larger molecular weight will not only increase the viscosity of hemoglobin solution so as to be a blood plasma substitute during blood transfusions, but also enhance the nitric oxide release rate by increasing the shear stress applied on the endothelium.

BRIEF DESCRIPTION OF THE DRAWINGS

The present invention will be apparent to those skilled in the art by reading the following detailed description of a preferred embodiment thereof, with reference to the attached drawings, in which.

The FIG. 3 is a schematic view illustrating the result of the hemoglobin composition in accordance with the present invention which has been processed by SDS polyacrylamide gel electrophoresis after column chromatography. In this diagram, lane "α-α Hb" represents the hemoglobin with α-α chains cross-linked; lane "Hb" represents unmodified hemoglobin; lane "p-Hb" represents the [Peptide-PEG-hemoglobin] which hasn't been purified by column chromatography; lane "A" represents the peak 1 fraction (i.e. [Peptide-PEG-hemoglobin]) collected from column chromatography process; lane "B" represents the peak 2 fraction (i.e. [Peptide-PEG-hemoglobin]) collected form column chromatography process; lane "C" represents the peak 3 fraction (i.e. hemoglobin unlinked to the peptide comprising SEQ ID NO: 1 through MAL-PEG-NHS) collected from column chromatography process; lane "D" represents the hemoglobin composition polymerized of the molecules from the peak 1 fraction (lane "A") with SPA-PEG-SPA followed by purification; lane "E" represents the hemoglobin composition polymerized of the molecules from the peak 2 fraction (lane "B") with SPA-PEG-SPA followed by purification.

DETAILED DESCRIPTION OF THE PREFERRED EMBODIMENT

Before preparation of the modified hemoglobin with an allosteric effector conjugated according to the present invention, it needs firstly to purify the hemoglobin from the blood, and it also needs to prepare the peptide comprising SEQ ID NO: 1 with a function as an oxygen regulatory factor, and the MAL-PEG-NHS used for conjugating the former two objects as well. While under crosslinking reactions, the MAL-PEG- NHS were conjugated with the peptide at first, followed by the conjugation of the product designated [Peptide-PEG-NHS] obtained from previous reaction with the hemoglobin, and finally the hemoglobin composition designated [Peptide-PEG-hemoglobin] was obtained.

Figure 1:
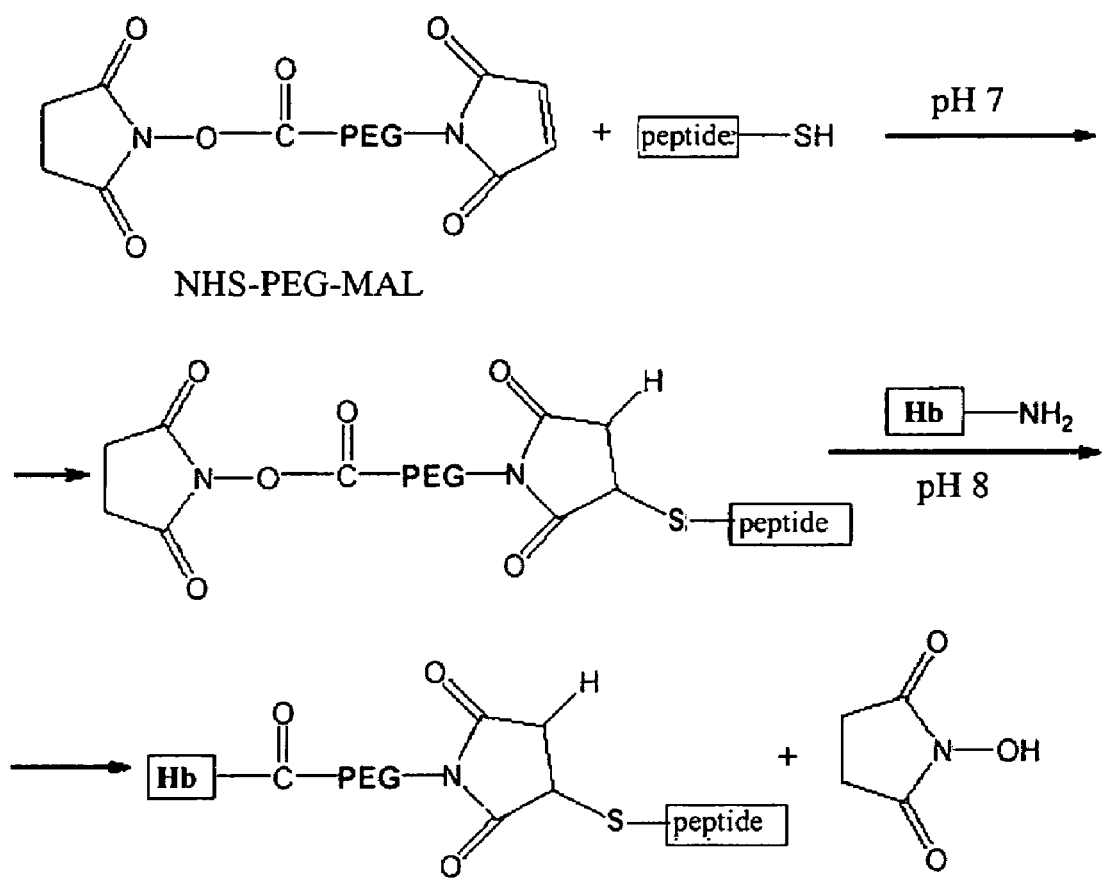
FIG. 1 is a schematic view showing the linkage of hemoglobin composition in accordance with the present invention.

With reference to FIG. 1, it is a schematic view showing the linkage of hemoglobin composition in accordance with the present invention. Under the preparation process, the MAL-PEG-NHS was firstly reacted with the peptide comprising SEQ ID NO: 1. Owing to a thio group (SH—) contained in the cysteine of the peptide, we could utilize the thio group to react with the functional group (MAL) in the MAL-PEG-NHS so as to yield a product of [Peptide-PEG-NHS], and then the [Peptide-PEG-NHS] was further reacted with the hemoglobin. The lysine residue contained on the surface of hemoglobin molecule was conjugated with the functional group, N-hydroxysuccinimidyl (NHS), in the [Peptide-PEG-NHS] and a hemoglobin composition of the [Peptide-PEG-hemoglobin] was finally yielded. The crosslinking site of lysine residue of the hemoglobin may belong to the β chain contained therein, and/or be but not limit to the 95th amino acid of the β chain.

The hemoglobin composition of the [Peptide-PEG-hemoglobin] in accordance with the present invention, the peptide thereof was able to enter into the central cavity formed between β-β chains due to the characteristic that the peptide was a part of a oxygen regulatory factor, which is used to regulate oxygen release efficiency, hence is able to regulate the oxygen release efficiency of the hemoglobin.

In addition to the increase in the efficiency of oxygen release for the hemoglobin, the present invention further provides a kind of hemoglobin composition which is either intra-crosslinked between subunits of each hemoglobin molecule, or inter-crosslinked between different hemoglobin molecules by means of a SPA-PEG-SPA so as to prevent the dissociation from hemoglobin tetramers. By crossbridging with the SPA-PEG-SPA, the modified hemoglobin [Peptide-PEG-hemoglobin] may further conjugate with the other modified or unmodified hemoglobin molecules, whereby the hemoglobin tetramer or a plurality of polymerized hemoglobin molecules were obtained consequently. After polymerization, by larger molecular weight of hemoglobin polymer, it would increase the viscosity of hemoglobin solution so as to be as a blood substitute for transfusion. On the other hand, also by the characteristic of the larger molecular weight of hemoglobin polymer, it is capable of increasing the release of nitric oxide by enhancing the shear stress applied to endothelium. The detailed description of the forgoing methods is as follows:

EXAMPLE 1

Purification of Hemoglobin 40 ml of human blood was obtained and placed into a vacuum blood collection tube containing ethylene diamine tetra acetic acid and then centrifuged at 800×g for 10 minutes. The supernatant and buffy coat were discarded, and the red blood cells in the lower layer were recovered. The red blood cells were washed repeatedly with physiological salt solution and centrifuged three times to remove buffy coat in the upper layer. 40 ml of red blood cell suspension (hematocrit 0.5) was subjected to gel filtration on a cellulose column to remove leukocytes. The purified red blood cell was broken by the method of frozen-thawed and separated by centrifugation at 12,000 rpm (Sorvall SS-34 rotor), 4 for 40 minutes. The cell membrane in the lower layer of suspension was discarded, and the upper layer suspension containing the hemoglobin was collected. The hemoglobin collected was further purified on a 1.5×2.5 cm Sephadex G-25 column so as to remove small molecules such as 2,3-DPG etc., and the purity of the hemoglobin was greater than 95%.

EXAMPLE 2

Preparation of [Peptide-PEG-NHS]

The peptide comprising SEQ ID NO: 1 was obtained by the prior typical synthesis means. The peptide comprising SEQ ID NO: 1 includes former 7 amino acids (MEELQDD) from N-terminus of human erythrocytic band 3 protein, and one cysteine and one glutamic acid added sequentially in C terminus thereof.

The reason why the present invention utilizes this kind of peptide is that the peptide comprising SEQ ID NO: 1 is part of a peptide chain of an oxygen regulatory factor capable of entering into the central cavity formed between β-β chains in hemoglobin, and with the effect for regulating the rate of oxygen release.

The linker used to conjugate the peptide comprising SEQ ID NO: 1 with the hemoglobin in accordance with the present invention is a kind of PEG derivative, maleimide-PEG-N-hydroxysuccinimidyl (hereinafter referred to as MAL-PEG-NHS) which comprises the PEG extended with two functional groups and has a molecular weight of 3,400 daltons.

At first, 0.398 mg of deoxygenated peptide comprising SEQ ID NO: 1 and 1.175 mg of MAL-PEG-NHS (wherein, the molar ratio of the peptide to MAL-PEG-NHS was 1.2:1) were prepared and reacted together in 20 μl, 10 mM of the deoxygenated HEPES (N-[2-Hydroxy ethyl]piperazine-N'-[2-ethane sulfonic acid]) buffer, pH 7.0, for about 1 to 30 minutes.

Due to the negative charge of glutamic acid residue contained in the peptide, the peptide was bended by the rejection raised from amino acids with negative electricity charge too near the N terminus of the peptide, thereby the cysteine residue on that peptide was exposed, and could be reacted to MAL function group contained in MAL-PEG-NHS so as to produce the composition designated [Peptide-PEG-NHS] consequently.

For preventing the MAL contained in MAL-PEG-NHS, which hasn't been linked yet, from being linked with cysteine residue of the hemoglobin in following reaction, it is necessary to deactivate those unreacted MAL function groups. As regards deactivation, 20 μl, 10 mM of cysteine (final concentration was 1 mM), pH 7.0, was added to the products preceded after previous reaction, and reacted for about 1 to 5 minutes. By this way, the unreacted MAL functional groups will be blocked by the conjugation with cysteine, and will not link to the cysteine of the hemoglobin added in following reaction, and be applicable to ensure yielding the desired hemoglobin composition.

EXAMPLE 3

Preparation of [Peptide-PEG-hemoglobin]

Firstly, a 288 µM, pH 8.0 of the purified hemoglobin solution from Example 1 (dissolved in 20 mM of HEPES buffer, pH 8.0) was prepared and purged with argon gas for about one hour to make the hemoglobin deoxygenated. Afterward, the [Peptide-PEG-NHS] solution prepared in the Example 2 was sucked by an airtight syringe, and then added along the tube wall into 1 ml deoxygenated hemoglobin solution obtained from the previous purification process (the molar ration of the [Peptide-PEG-NHS] to deoxygenated hemoglobin solution is 1.2:1). The solution was then stirred slightly under room temperature for 1-2 hours, so that the [Peptide-PEG-NHS] could react with the hemoglobin via the NHS functional group thereof. As regards the hemoglobin, it was reacted with the NHS functional group via the lysine residue exposed on the outer surface of the subunits thereof. After analysis, it was found that the lysine residue reacted was in the β chain of the hemoglobin, and was particularly positioned at the lysine 95.

With utilization of the composition of [Peptide-PEG-hemoglobin] in accordance with the present invention, wherein the MAL-PEG-NHS can act as an extensible arm working between the peptide and the hemoglobin, and make the possibility for the peptide comprising SEQ ID NO: 1, which with effects as a regulatory factor, entering into the central cavity formed between β-β chains of the hemoglobin, and further make the hemoglobin having an enhanced efficiency of oxygen release in appropriate circumstance.

Figure 2:
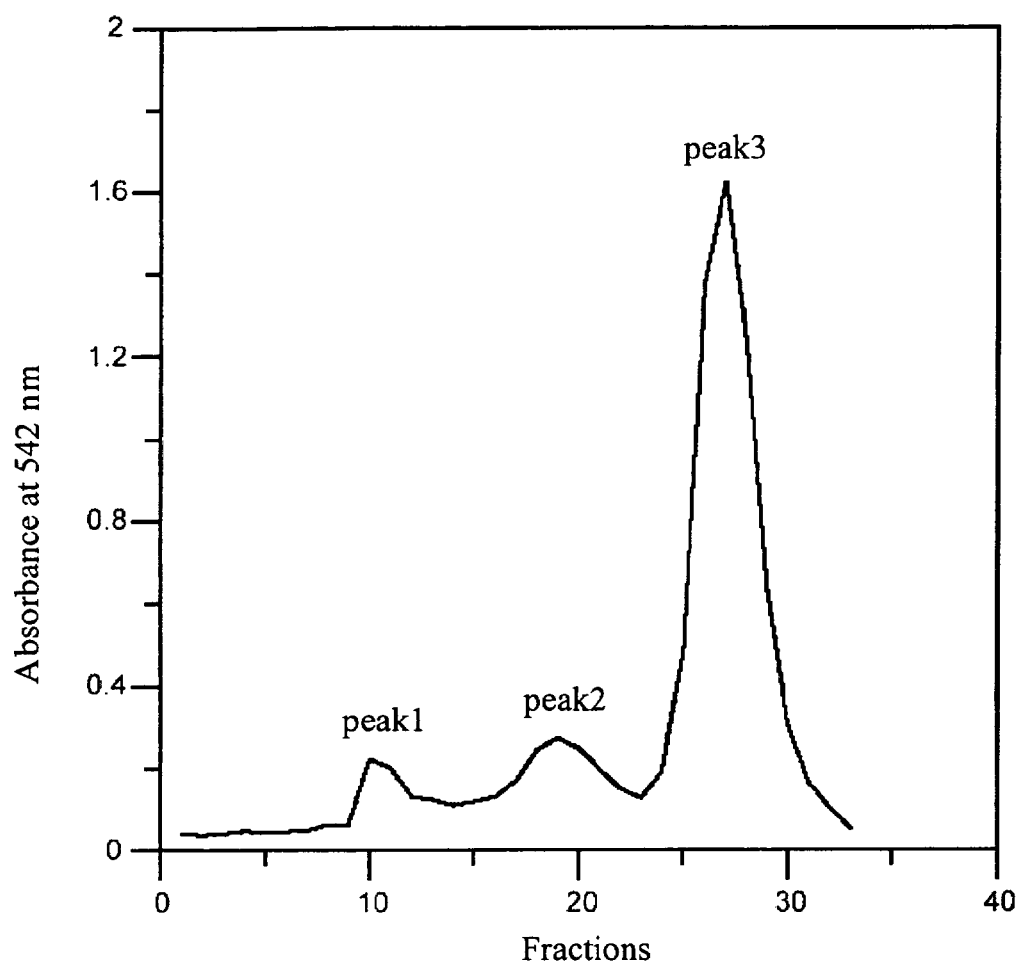
FIG. 2 is a schematic view illustrating the analysis of the Peptide-PEG-hemoglobin product followed by purification on CM-sepharose column in accordance with the present invention. During the process of purification and separation, 0.5 ml composition is collected each fraction and wherein the hemoglobin is as detected of absorbance at wavelength 542 nm. Among them, the 10th~13th fractions are collected as the peak 1 fraction, the 18th~21st fractions are collected as the peak 2 fraction, and the 26th~28th fractions are collected as the peak 3 fraction;.

The [Peptide-PEG-hemoglobin] solution prepared according to the present invention can be purified by means of the CM-sepharose column, whereat the result of purification is illustrated in FIG. 2. During the process of separation and purification, 0.5 ml of solution was collected each fraction, wherein the hemoglobin was as detected of absorbance at wavelength 542 nm. Among them, the 10th~13th fractions are collected as the peak 1 fraction, the 18th~21st fractions are collected as the peak 2 fraction, and the 26th~28th fractions are collected as the peak 3 fraction.

The hemoglobin been purified, can further be confirmed and analyzed by the SDS polyacrylamide gel electrophoresis. Also referring to the FIG. 3, it is a schematic view illustrating the result of the hemoglobin, which has been processed by SDS polyacrylamide gel electrophoresis after column chromatography. In this diagram, the marker for 16 kD is approximately the molecular weight of hemoglobin monomer, and 32 kD is approximately the molecular weight of hemoglobin dimer. Where lane "α-α Hb" indicates the hemoglobin with α-α chain cross-linked; lane "Hb" represents the unmodified hemoglobin, wherein the band near 16 kD marker indicating the unmodified heoglobin monomer (i.e. subunit); lane "p-Hb" represents the unpurified [Peptide-PEG-hemoglobin], wherein the band near 16 kD marker indicating the α chain or the β chain which still hasn't been linked by the MAL-PEG-NHS, and the band positioned between 16 kD and 32 kD is the composition of [Peptide-PEG-one subunit of hemoglobin], which is namely the modified hemoglobin composition in accordance with the present invention. Lane "A" represents the peak 1 fraction been purified by column chromatography; lane "B" represents the peak 2 fraction been purified by column chromatography. The band in-between the 16 kD and 32 kD of lane "A" and "B" has been verified as the composition of [Peptide-PEG-one subunit of hemoglobin] with Matrix Assisted Laser Desorption Ionisation/TIME-of-Flight Mass Spectrometry (MALDI-TOF MS), and further more, analyzed by Two-Dimensional Gel Electrophoresis (2D-GE) (data not shown). It was found that in peak 1 fraction the peptide was primarily linked to the β chain of hemoglobin, whereas in peak 2 fraction the peptide was primarily linked to the α chain of hemoglobin. Lane "C" represents the peak 3 fraction been purified by column chromatography, wherein there wasn't any band positioned in-between the marker of 16 kD and 32 kD, therefore the band near 16 kD indicating the kind of hemoglobin (α chain or β chain) linked without the peptide comprising SEQ ID NO: 1 by MAL-PEG-NHS.

Figure 4:
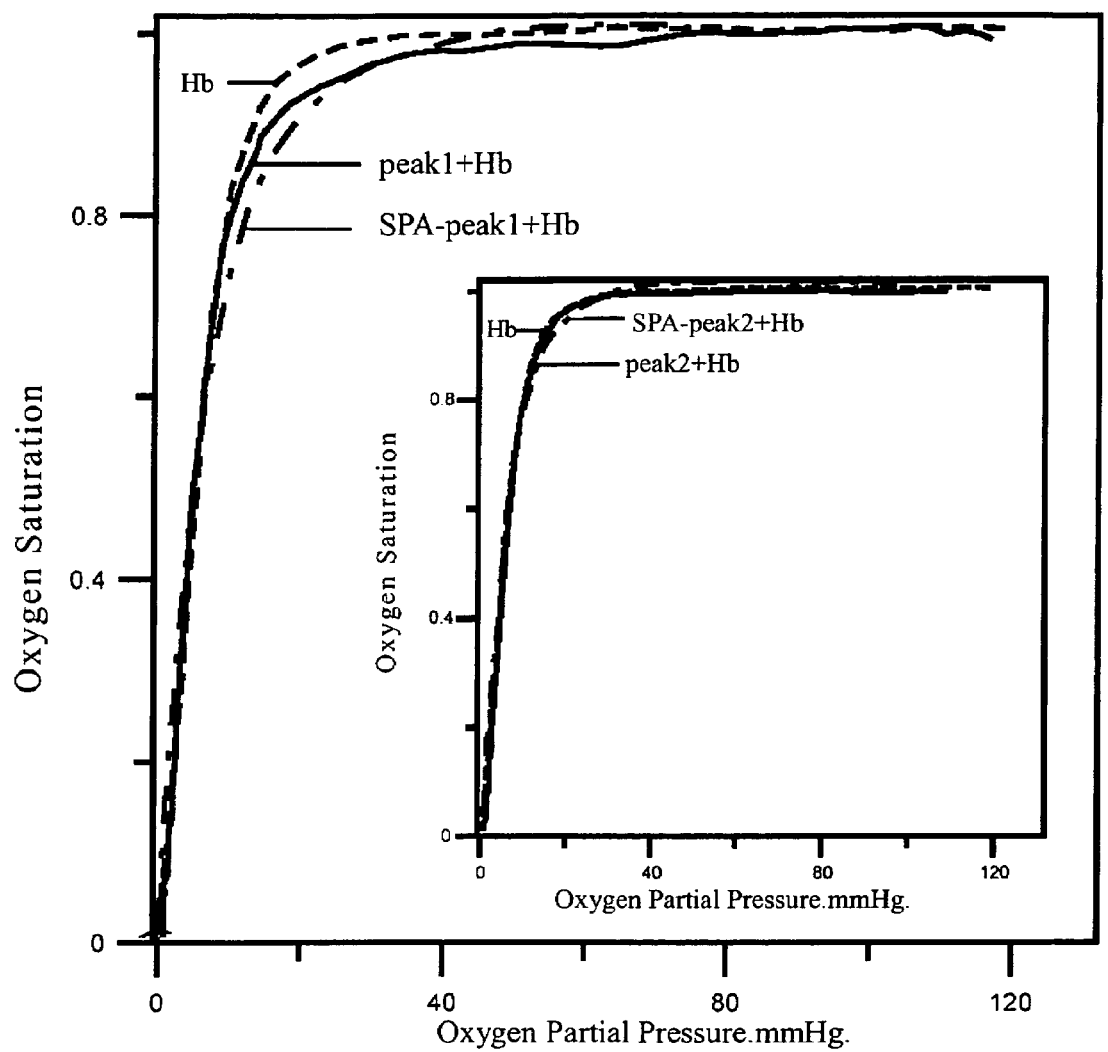
FIG. 4 is an oxygen dissociation curve plot for different types of the hemoglobin molecules. The ordinate of plot indicates the oxygen saturation of the hemoglobin, and the abscissa represents the partial pressure of oxygen. In this diagram, "- - - "(Hb) represents unmodified hemoglobin; " "(peak 1+Hb) represents th ptide-PEG-hemoglobin] provided in the present invention (i.e. peak 1) mixed with Hb in a molar ratio of 1:1; " "(peak 2+Hb) represents the [Peptide-PEG-globin] provided in the present invention (i.e. peak 2 fraction) mixed with Hb in a molar ratio of 1:1; " "(SPA-peak 1+Hb) represents the peak 1 fraction being purified mixed with Hb in a ratio of 1:1, and followed by polymerization with SPA-PEG-SPA; " "(SPA-peak 2+Hb) represents the peak 2 fraction being purified mixed with Hb in a ratio of 1:1, and followed by polymerization with SPA-PEG-SPA.

With the reference to FIG. 4, it is an oxygen dissociation curve plot for different types of hemoglobin. The oxygen dissociation curve herein can be obtained with the utilization of protocatechuic acid/protocatechuic acid 3,4-dioxygenase (PCA/PCD), micro oxygen electrode, and ultraviolet/visible spectrometer. In this diagram, the ordinate indicates the saturation level of oxygenated hemoglobin, and the abscissa indicates the oxygen partial pressure. Among them, "- - -"(Hb) indicates the unmodified hemoglobin; "——"(peak 1+Hb) indicates the result that the [Peptide-PEG-hemoglobin proposed], collected in peak 1 fraction, in the present invention was mixed with unmodified Hb in a molar ratio of 1:1; "——"(peak 2+Hb) indicates the result that the [Peptide-PEG-hemoglobin], collected in peak 2 fraction, in the present invention was mixed with unmodified Hb (Hb) in a molar ratio of 1:1.

According to FIG. 4, it is found that the "peak 1+Hb" has a lower oxygen affinity than unmodified hemoglobin (Hb). Therefore, the hemoglobin composition from peak 1 fraction (i.e. [Peptide-PEG-hemoglobin]) has a higher feasibility to release oxygen than that of unmodified hemoglobin (Hb). In comparison, the curve of "peak 2+Hb" is nearly matching with the unmodified hemoglobin (Hb), however the hemoglobin composition from peak 2 fraction still has lower oxygen affinity than unmodified hemoglobin (Hb). Thus, by the analysis of oxygen dissociation curve, it is confirmed that the composition of [Peptide-PEG-hemoglobin] in accordance with the present invention, particularly the hemoglobin composition with peptide linked to the β chain thereof (namely peak 1), does has an effect to increase the oxygen release rate of the hemoglobin by decreasing the affinity of oxygen to the hemoglobin namely.

EXAMPLE 4

Crosslinking of the [Peptide-PEG-hemoglobin] with Other Hemoglobin Molecules

With the utilization of the composition of [Peptide-PEG-hemoglobin] according to the present invention, it is applicable to enhance oxygen release easily under appropriate circumstance and with a higher deoxygenating ability. In order to further prevent hemoglobin molecules been dissociated from tetramer into dimers, and to avoid any side effects such as renal function, high blood pressure etc., the present invention herein may further utilize another kind of linker to crosslink among the subunits of hemoglobin or among the molecules of hemoglobin so as to form a larger molecule and increase the viscosity of the hemoglobin, and also increase the shear stress on the endothelium so that the nitric oxide release rate is increased accordingly.

Firstly, the purified [Peptide-PEG-hemoglobin] prepared from Example 3 was mixed with unmodified hemoglobin at a molar ratio of 1:1 in room temperature for one hour. Afterward, it was dialysis with 400 ml, 20 mM of HEPES buffer, pH 8.0, three times for total 24 hours. 0.342 mg of SPA-PEG-SPA was prepared and reacted with argon gas for 10 minutes for deoxygenation, and then 100 μl, 5 mM of deoxygenated HEPES buffer, pH 7.0, was added and reacted for 1 minute for the SPA-PEG-SP to be dissolved. An airtight syringe was used to suck deoxygenated SPA-PEG-SPA solution, the solution was then added along the tube wall into the mixed solution prepared from 1.7 ml, 7.25 μM of the [Peptide-PEG-hemoglobin], pH8.0, mixed with unmodified hemoglobin (the molar ration of hemoglobin to SPA-PEG-SPA was 1:8), and was stirred slightly under room temperature for 1 hour, so that the SPA-PEG-SPA was capable of crosslinking among inter-hemoglobin molecules or intra-hemoglobin molecule, thereby a hemoglobin tetramer and/or a partial modified type hemoglobin compositions with a plurality of molecules of hemoglobin tetramer polymerized were obtained (part of the hemoglobin molecules were modified).

Additionally, the SPA-PEG-SPA can also be used to link among the [Peptide-PEG-hemoglobin] molecules or among the subunits of the hemoglobin thereof according to the present invention so as to form a hemoglobin tetramer and/or a kind of complete modified type hemoglobin compositions with a plurality of molecules of hemoglobin tetramer polymerized. In this way, each hemoglobin molecule was modified with the peptide conjugated so that it is applicable to achieve the optimum efficiency of oxygen release.

Figure 3:
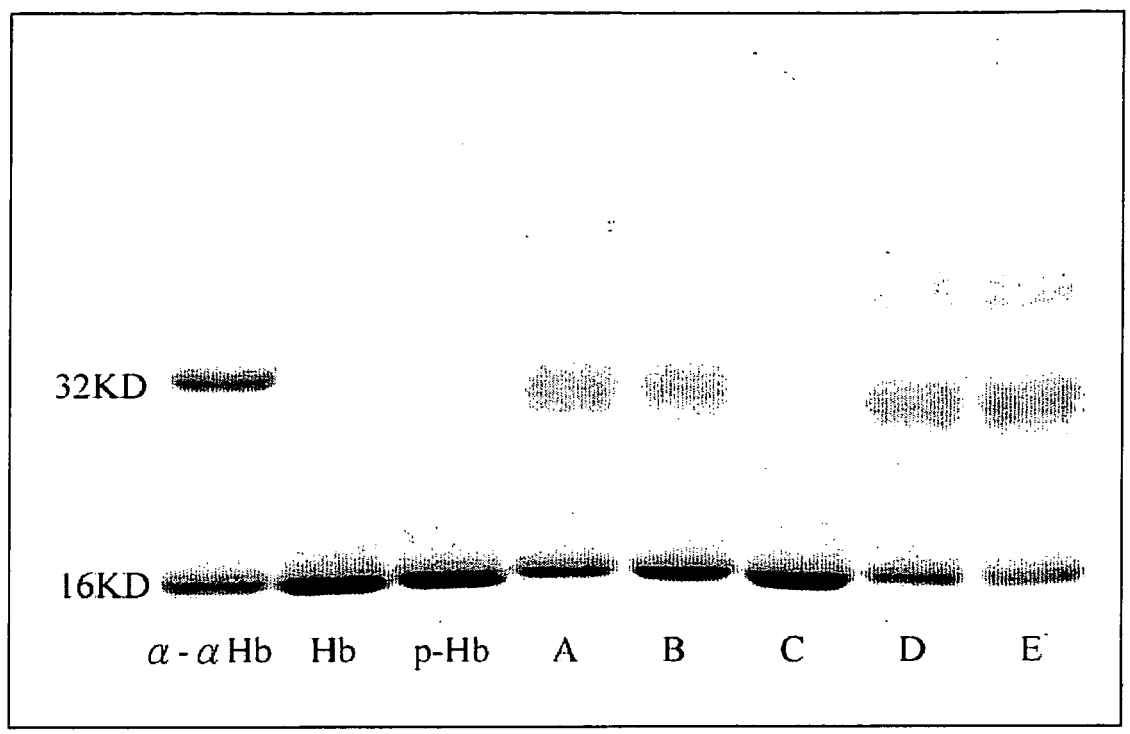

The products of the hemoglobin crosslinked by SPA-PEG-SPA were referred to FIG. 3. In this diagram, lane "D" represents the analysis result of linkage between the mixture of SPA-PEG-SPA and peak 1 fraction (i.e. [Peptide-PEG-hemoglobin]) with the unmodified hemoglobin, and the lane "E" represents the analysis result of the linkage between the mixture of SPA-PEG-SPA and peak 2 fraction (i.e. [Peptide-PEG-hemoglobin]) with the unmodified hemoglobin. It is found, from the relevant diagram, that the product yielded either in the lane "D" or "E", there existed a 16 kD (hemoglobin monomer) and a 32 kD (hemoglobin dimer) band. Moreover, there is still existed a composition larger than 32 kD, and the composition is namely the hemoglobin tetramer or/and hemoglobin polymer formed by the SPA-PEG-SPA crosslinkage. Therefore, with the crosslinkage of the SPA-PEG-SPA, subunits of hemoglobin could be crosslinked with each other, and hemoglobin molecules could also be inter-crosslinked therebetween in the meanwhile, so that the majority of subunits contained in the hemoglobin were capable of forming the tetramer conformation and consequently avoided the drawbacks of the known hemoglobin being dissociated easily into dimers in human body and prevent physical defects accordingly.

With the reference to FIG. 4 again, it is an oxygen dissociation curve plot of the hemoglobin polymer conjugated by means of SPA-PEG-SPA. In this diagram, the "-•-•-•"(SPA-peak 1+pHb) represents the hemoglobin composition collected from the peak 1 fraction, which was purified and mixed with Hb (unmodified hemoglobin) in a molar ratio of 1:1, and then fowllowed by polymerization with SPA-PEG-SPA; the "-•-•-•"(SPA-peak 2+pHb) indicates the hemoglobin composition collected from the peak 2 fraction, which was purified and mixed with Hb (unmodified hemoglobin) in a molar ratio of 1:1, and then followed by polymerization with SPA-PEG-SPA.

It was found from the diagram, that the oxygen affinity in "SPA-peak 1+Hb" was similar to that of the "peak 1+Hb", but both of them the oxygen affinity was still lower than that of the unmodified hemoglobin. Moreover, the oxygen affinity in "SPA-peak 2+Hb" was lower than that of the unmodified hemoglobin as well (despite the variance is less if comparing to either the "SPA-peak 1+Hb" or the "peak 1+Hb"). Therefore, the modified hemoglobin with an allosteric effector conjugated utilizing the above-mentioned method according to the present invention, by means of conjugation of the peptide comprising SEQ ID NO: 1 via the MAL-PEG-NHS, whether it is crosslinked to form a tetramer or a polymer with SPA-PEG-SPA, had a superior ability of deoxygenation than that of the unmodified hemoglobin, Thus, the modified hemoglobin with an allosteric effector conjugated provided by the present invention can be used as a well blood substitute of known hemoglobin solution.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A modified hemoglobin conjugated with an allosteric effector comprising:
   a hemoglobin composition prepared by conjugating a peptide comprising SEQ ID NO: 1 on a hemoglobin through a maleimide-PEG-N-hydroxysuccinimidyl under a deoxy condition;
   wherein, the peptide comprising SEQ ID NO: 1 is bonded via the cysteine residue therein through the maleimide functional group contained in the maleimide-PEG-N-hydroxysuccinimidyl under a deoxy condition, and the hemoglobin is bonded via the lysine residue on the surface through the N-hydroxysuccinimidyl functional group contained in the maleimide-PEG-N-hydroxysuccinimidyl under a deoxy condition.

2. The modified hemoglobin of claim 1, wherein the hemoglobin composition is further crosslinked by a succinimidyl propionate-PEG-succinimidyl propionate to form an intra-crosslinked hemoglobin tetramer.

3. The modified hemoglobin of claim 2, wherein the intra-crosslinked hemoglobin tetramer is further crosslinked among inter-molecules by the succinimidyl propionate-PEG-succinimidyl propionate to form a modified hemoglobin composition having a plurality of the intra-crosslinked hemoglobin tetramer molecules polymerized.

4. The modified hemoglobin of claim 1, wherein the lysine residue on the surface of the hemoglobin is in the β chain.

5. The modified hemoglobin of claim 4, wherein the lysine residue on the surface of the hemoglobin is the 95th amino acid of the β chain.

* * * * *

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Chemically Synthesized

```
<400> SEQUENCE: 1

Met Glu Glu Leu Gln Asp Asp Cys Glu
1               5
```